United States Patent
Morris et al.

[11] Patent Number: 5,923,001
[45] Date of Patent: Jul. 13, 1999

[54] AUTOMATIC SURGICAL SPONGE COUNTER AND BLOOD LOSS DETERMINATION SYSTEM

[75] Inventors: Sharon L. Morris; Dean E. Morris, both of Abita Springs, La.

[73] Assignee: Surgical Resources, L.L.C., Covington, La.

[21] Appl. No.: 08/833,387

[22] Filed: Apr. 4, 1997

Related U.S. Application Data

[63] Continuation-in-part of application No. PCT/US95/09094, Jul. 19, 1995, which is a continuation of application No. 08/286,413, Aug. 5, 1994, Pat. No. 5,650,596.

[51] Int. Cl.$^6$ .................... G01G 19/22; A61M 1/00
[52] U.S. Cl. .................... 177/245; 604/317; 177/25.17
[58] Field of Search .................... 177/15, 25.13, 177/25.19, 45, 245, 25.17; 604/317, 318, 403, 404, 407; 340/572, 573

[56] References Cited

U.S. PATENT DOCUMENTS

| | | | |
|---|---|---|---|
| 3,367,431 | 2/1968 | Baker | 177/245 |
| 3,675,190 | 7/1972 | Auer, Jr. et al. | 340/1 |
| 4,193,405 | 3/1980 | Abels | 128/296 |
| 4,213,197 | 7/1980 | Magori | 367/94 |
| 4,289,032 | 9/1981 | Tominaga et al. | 73/599 |
| 4,295,537 | 10/1981 | McAvinn et al. | 177/15 |
| 4,422,548 | 12/1983 | Cheesman et al. | 177/245 |
| 4,498,076 | 2/1985 | Lichtblan | 340/572 |
| 4,510,489 | 4/1985 | Anderson, III et al. | 340/572 |
| 4,650,464 | 3/1987 | Ruiz et al. | 604/49 |
| 4,658,818 | 4/1987 | Miller, Jr. et al. | 128/303.1 |
| 4,832,198 | 5/1989 | Alikhan | 206/438 |
| 4,887,715 | 12/1989 | Spahn et al. | 206/370 |
| 4,889,230 | 12/1989 | Zachry | 206/362 |
| 4,903,837 | 2/1990 | Duello | 206/440 |
| 4,922,922 | 5/1990 | Pollock et al. | 128/760 |
| 5,009,275 | 4/1991 | Sheehan | 117/25.13 |
| 5,031,642 | 7/1991 | Nosek | 128/906 |
| 5,057,095 | 10/1991 | Fabian | 604/362 |
| 5,103,210 | 4/1992 | Rode et al. | 340/572 |
| 5,107,862 | 4/1992 | Fabian et al. | 128/899 |
| 5,186,322 | 2/1993 | Harreld et al. | 206/216 |
| 5,188,126 | 2/1993 | Fabian et al. | 128/899 |
| 5,190,059 | 3/1993 | Fabian et al. | 128/899 |
| 5,300,120 | 4/1994 | Knapp et al. | 623/11 |
| 5,329,944 | 7/1994 | Fabian et al. | 128/899 |
| 5,353,011 | 10/1994 | Wheeler et al. | 340/572 |
| 5,357,240 | 10/1994 | Sanford et al. | 340/572 |
| 5,381,137 | 1/1995 | Ghaem et al. | 340/572 |
| 5,460,178 | 10/1995 | Hudin et al. | 128/660.07 |
| 5,491,468 | 2/1996 | Everett et al. | 340/572 |
| 5,650,596 | 7/1997 | Moris et al. | 177/25.13 |
| 5,689,239 | 11/1997 | Turner et al. | 340/572 |

*Primary Examiner*—Randy W. Gibson
*Attorney, Agent, or Firm*—Garvey, Smith, Nehrbass & Doody, L.L.C.

[57] ABSTRACT

A surgical sponge detection system includes a plurality of surgical sponges (2) having radio frequency identification tags (1) securely attached thereto and a non-optical hand-held reader (40) for detecting the sponges by detecting the tags (1). Also disclosed is a device (30) for automatically counting, weighing, and calculating blood loss contained within, soiled surgical sponges (2) which includes a cabinet with an opening (3) at the top through which sponges (2) are deposited, a reader (6) which scans each sponge (2) entered and determines sponge type from a tag (1) affixed to each sponge (2), and a disposable bag (8) into which the sponges (2) are deposited. The disposable bag (8) is removably mounted to a weighing scale (10); there is also a rear door (9) from which the disposable bag (8) can be easily removed, a rechargeable battery (11), a shelf (12) for unused disposable bag storage, a control unit (4) which processes data received from reader (6) and scale (10) and instantaneously calculates total weight of liquid contained within sponges entered, a display panel (5) continuously displays the number and type of sponges entered during a given procedure as well as the total weight of liquids retained in those sponges. There is a means for automatically determining the weight of the sponges when dry which includes a non-optical scanner means (6) which can read an indicating means (1) on the sponges (2) even when the indicating means (1) is covered with blood or other body fluids.

8 Claims, 6 Drawing Sheets

AUTOMATIC SURGICAL SPONGE COUNTER AND BLOOD LOSS DETERMINATION SYSTEM

CROSS-REFERENCE TO RELATED APPLICATIONS

This is a continuation-in-part of International Application Number PCT/US95/09094, filed Jul. 19, 1995, which is a continuation of U.S. patent application Ser. No. 08/286,413, filed Aug. 5, 1994, U.S. Pat. No. 5,650,596, both hereby incorporated by reference.

STATEMENT REGARDING FEDERALLY SPONSORED RESEARCH OR DEVELOPMENT

Not applicable

REFERENCE TO A "MICROFICHE APPENDIX"

Not applicable

BACKGROUND OF THE INVENTION

1. Field of the Invention

The present invention relates to devices which detect, collect, weigh and count surgical sponges. The present invention also relates to surgical sponges which can be detected non-optically.

2. General Background of the Invention

During surgery absorbent sponges are used to soak up blood and other body fluids in and around the incision site. Because the risk of a sponge being retained inside a patient is so great, surgical personnel go to great lengths to account for each and every sponge which is used in surgery. Strict sponge count policies have been developed by hospitals to deal with this issue. Moreover, surgeons and anesthesiologists determine blood loss by using visual inspection or the manual weighing of soiled sponges, thus soiled sponges are usually kept in one area of the operating room. Another area of concern regarding soiled surgical sponges is the risk of transmission of bloodborne diseases such as hepatitis B virus (HBV) and human immunodeficiency virus (HIV). To reduce exposure and contamination every precaution necessary should be taken to reduce risk of infection.

Sponge counts are an essential part of operating room procedure. They help ensure patient safety by reducing the chance that a sponge will be retained inside of the patient. Typical sponge count policies include: an initial count at the beginning of a procedure and subsequent counts throughout the procedure when additional sponges are added to the sterile field, before the closure of a deep incision, after the closure of a body cavity, when scrub or circulating personnel are relieved, and before the procedure is completed.

In addition, it is necessary for the anesthesiologist and surgeon to have an accurate measurement of blood loss contained in sponges, so that if excessive blood loss is occurring, blood components can be ordered and administered immediately. This information is provided by weighing soiled sponges and then subtracting the dry weight of the number of sponges weighed from the total.

Moreover, soiled sponges are a source of contamination, thus handling and exposure should be kept to a minimum. Procedures which reduce the transmission of bloodborne pathogens include making sure that soiled sponges are handled with gloves and instruments only and that used soiled sponges are appropriately contained and confined.

In 1992, the Occupational Safety and Health Administration (OSHA) issued new regulations regarding bloodborne pathogens in U.S. hospitals. Nearly 6 million healthcare workers in the United States who could be "reasonably anticipated" to come in contact with blood and other body fluids are subject to the new regulations. These regulations are intended to reduce worker exposure to hepatitis B virus (HBV), human immunodeficiency virus (HIV), or other bloodborne pathogens. Under the section on Engineering and Work Practice Controls, hospitals are required to eliminate or minimize employee exposure. This includes the implementation of new designs for devices which count sutures and sponges.

For more information about surgical sponge handling and counting, please see U.S. Pat. No. 4,422,548, incorporated herein by reference.

U.S. Pat. No. 3,367,431 discloses a device for automatically counting and weighing surgical sponges. However, the device cannot distinguish between different sponges. Also, the amount of blood contained in soiled sponges must be manually calculated. Further, it does not use removable disposable bags.

U.S. Pat. No. 4,295,537 discloses a sponge-collecting device that keeps count and determines the weight of blood-soaked sponges. However, the device cannot automatically distinguish between different sponges. Also, the device does not automatically count the sponges (the number and dry weight of the sponges must be manually input).

U.S. Pat. No. 4,422,548 discloses a sponge-collecting device that determines the weight of blood-soaked sponges. However, the device cannot automatically distinguish between different types of sponges. It also cannot determine the amount of blood in the sponges.

U.S. Pat. No. 5,009,275 discloses a sponge-collecting device that determines the weight of blood-soaked sponges. However, the device cannot automatically distinguish between different types of sponges, and so it cannot automatically determine the amount of blood loss when sponges of different dry weights are collected in the container.

Radio Frequency Identification Systems are based on two principle components, a passive tag or transponder and a hand held or stationary reader. In operation, the hand held or stationary reader emits a low frequency magnetic field, which activates the passive tag or transponder within its range. The passive tag has no power source of its own. It derives the energy needed for operation from the magnetic field generated by the reader. Because the tags have no power source of their own, the only limitation to the operational lifespan of the tag is the durability of its protective encapsulation, usually, but not limited to, plastic or glass. Tags are available in many shapes and sizes, each designed for the unique rigors and requirements of specific applications. RF tags operate by proximity as opposed to optics like a bar code. As a result they can be read in harsh environments, submerged in liquids and can be read spherically from any direction, through most materials. They can be read through tissue, bone, etc.

Also of potential interest are the following U.S Pat. Nos.: 3,367,431; 4,193,405; 4,498,076; 4,510,489; 4,658,818; 4,922,922; 5,031,642; 5,057,095; 5,103,210; 5,188,126; 5,190,059; 5,300,120; 5,329,944; 5,353,011; 5,357,240; 5,381,137; all patents cited in the file of U.S. patent application Ser. No. 08/286,413.

SUMMARY OF THE INVENTION

The present invention involves the use of radio frequency identification (RF ID) tags on surgical sponges and two related medical devices which will be used to identify and track those sponges during surgery. RF technology was chosen by the present inventors because no other technology available offers the reliability, accuracy and performance demanded by the operating room environment. The first device, a hand-held reader, will be passed over the surgical wound prior to the closing of the wound by the surgeon. The hand-held reader will then identify any sponges which may have been inadvertently left in the wound, thus preventing the retention of sponges inside of the patient. This hand-held reader can be used during all surgical procedures and will eliminate the dangerous and time consuming task of manually counting and bagging soiled sponges. The second device, a sponge management system including a counting, weighing, and calculating device for automatically counting and weighing surgical sponges and determining the amount of blood contained therein, will be utilized during procedures in which determination of blood contained in sponges is important. These procedures include; any procedure involving small children or infants, and heavy blood loss procedures such as cardiovascular, transplants, and obstetrical. During surgery all soiled sponges, regardless of size, will be deposited into the counting, weighing, and calculating device where the device will then determine the amount of blood contained in those sponges and display this amount on a liquid crystal display panel. In addition, the counting, weighing, and calculating device will automatically bag those sponges and give a visible running count of each type of sponge deposited. The hand-held reader will be an attachment used with the counting, weighing, and calculating device to be used at the time of closure to assure that a sponge is not retained in the patient. The use of RF tagged sponges and the accompanying identification systems discussed will have a tremendous impact on operating rooms worldwide.

RF tags can also be attached to surgical instruments that might accidentally get left in the human body during surgery to allow these surgical instruments to be detected non-optically.

As used herein, "non-optical detection" means detection of an object without visible light or X-rays. The preferred non-optical detection means comprises radio frequency (RF) scanners.

The apparatus of the present invention solves the problems confronted in the art in a simple and straightforward manner. What is provided is a device which automatically counts surgical sponges and automatically determines the amount of blood contained in the sponges, without any input or calculations during the surgery by any person. The apparatus includes means for automatically determining the weight of the sponges when dry, and for deducting that weight from the total weight of the sponges and blood in the apparatus. The soiled sponges will be held inside of the device in a removable disposable bag. Means are also provided to keep a running total of the number of sponges which have entered the apparatus from a predetermined time, and the total amount of blood which has entered the device from a predetermined time, even when a full bag is removed and replaced with an empty bag in order to make room for additional sponges to enter the container.

The means for automatically determining the weight of the sponges when dry includes a non-optical scanner means which can read an indicating means on the sponges even when the indicating means is covered with blood or other body fluids.

The present invention comprises a system for facilitating counting of surgical sponges and determining the approximate amount of body fluids contained therein. It includes a plurality of sponges of varying weights, each sponge having a dry weight before being used to absorb fluids and an indicating means thereon for indicating the dry weight of the sponge, the dry weight of the sponge including the weight of the indicating means; and a device for counting the surgical sponges and determining the approximate amount of body fluids contained therein. The device comprises a container means for containing the surgical sponges, the container means having an opening above a receptacle means for receiving the surgical sponges, scanner means for detecting when one of the surgical sponges passes through the opening, and detecting means for automatically determining the dry weight of the surgical sponges which have passed through the opening since a predetermined time by detecting the indicating means on the sponges. The device also includes calculating means for automatically determining the approximate amount of body fluid contained in the surgical sponges which have entered the container since a predetermined time by subtracting the dry weight of the sponges from the weight of the sponges including the body fluids. The device further comprises first display means for displaying an indication of the approximate amount of body fluid contained in the surgical sponges which have entered the container since a predetermined time, determining means for automatically determining the number of surgical sponges which have entered the container since a predetermined time, and second display means for displaying the number of surgical sponges which have entered the container since a predetermined time.

The detecting means is capable of distinguishing between multiple types of surgical sponges (and preferably detecting multiple sponges simultaneously and identifying them) even those sponges of different types but similar weights, and the second display means displays the number of each type of sponge which is received.

The first display means indicates, with an accuracy of ±0.1%, the exact amount of body fluids contained in the sponges which have entered the container since a predetermined time.

The detecting means comprises a non-optical scanner means which can read an indicating means on the sponges even when the indicating means is covered with blood or other body fluids.

There are three main differences between the Baker device (that shown and described in U.S. Pat. No. 3,367,431) and the apparatus of the present invention. The device of the present invention is superior and different in the following areas: the ability to distinguish between different types of sponges and to give a visible running count of each type; the ability to automatically calculate the amount of blood contained in soiled sponges; and the provision of removable disposable bags to minimize handling of the soiled surgical sponges.

The ability to distinguish between different types of sponges and maintain a running count of each type is a major advantage of the present invention over the Baker device. The Baker device can only give a running count of total sponges used. It cannot break that number down by type. In the case of a miscount, knowing the breakdown of different size sponges helps narrow down where the mistake was made. Several Baker devices would have to be used to equal one device of the present invention.

The ability to identify what type of sponge has entered the device is essential to calculating the amount of blood contained in the soiled sponges. Pre-programmed dry weights for each type of sponge allows instant computation by the device of the present invention. The device of the present invention can instantaneously calculate blood loss and also store in memory this amount when the disposable bag is removed, thereby maintaining a constant readout throughout the procedure. Although the Baker device weighs soiled sponges, the calculation is still done manually. This calculation is extremely complicated and time-consuming given the different size sponges used. Each successive calculation gets more complicated due to the zeroing device which is utilized to help give a constant reading. An accurate measurement is dependent on how often the circulator calculates blood loss. Add to this, the findings of an article on blood loss determination in the Official Journal of the Association of Operating Room Nurses, (AORN) for June 1981, volume 33, No. 7 by Darden, which suggests that sponge tallies and weighing of sponges should be made at least every 15 minutes, otherwise determination of blood loss may be quite inaccurate due to evaporation. By instantly calculating blood loss and then holding this amount in memory, the present invention eliminates these inaccuracies. In addition, potential human error in the calculation is also eliminated.

The third difference between the two devices is the presence of a removable disposable bag in the device of the present invention. This feature will drastically reduce the handling of soiled sponges and thus the exposure of staff to blood. This is extremely important given the risk of infection to AIDS. When a sponge enters the device, it is deposited into a disposable bag where it will stay until the bag is removed and sealed. The Baker device requires personnel to remove the soiled sponges from the basket and then bag them for disposal.

The present invention includes apparatus for helping to prevent surgical sponges from being inadvertently left in a patient after surgery comprising a non-optical scanner means, a plurality of surgical sponges, and a plurality of identification tags, wherein each surgical sponge has one of the identification tags securely attached thereto for allowing the sponge to be detected by the non-optical scanner means, and either the non-optical scanner means has means for detecting and identifying multiple identification tags simultaneously, or the tags can be encoded with identifying means to identify the type of sponge to which it is attached, or both. Preferably, the identification tags do not exceed one inch in diameter and 0.20 inches in thickness. The identification tags preferably do not exceed four grams in weight, and more preferably do not exceed three grams in weight. Preferably, the identification tag is a radio frequency identification tag and the non-optical scanner means is a radio frequency reader; the radio frequency reader preferably has a read range of at least 6 inches, more preferably at least 10 inches, and most preferably at least 15 inches, when used with the identification tags attached to the surgical sponges.

The present invention also includes a method of monitoring surgical sponges during and after surgery for helping to prevent surgical sponges from being inadvertently left in a patient after surgery, comprising the following steps:

using in a surgical wound only surgical sponges which each have an identification tag securely attached thereto for allowing the sponge to be detected by a non-optical scanner means;

using a non-optical scanner means to scan the surgical wound before closing the surgical wound, wherein either the non-optical scanner means has means for detecting and identifying multiple identification tags simultaneously, or the tags can be encoded with identifying means to identify the type of sponge to which it is attached, or both. Preferably, the identification tags do not exceed one inch in diameter and 0.20 inches in thickness. The identification tags preferably do not exceed four grams in weight, and more preferably do not exceed three grams in weight. Preferably, the identification tag is a radio frequency identification tag and the non-optical scanner means is a radio frequency reader; the radio frequency reader preferably has a read range of at least 6 inches, more preferably at least 10 inches, and most preferably at least 15 inches, when used with the identification tags attached to the surgical sponges.

The present invention also includes a system for facilitating detection of surgical sponges, counting of surgical sponges and determining the approximate amount of body fluids contained therein, comprising:

a plurality of sponges of varying weights, each sponge having a dry weight before being used to absorb fluids and an indicating means thereon for indicating the dry weight of the sponge, the dry weight of the sponge including the weight of the indicating means;

a device for counting the surgical sponges and determining the approximate amount of body fluids contained therein, comprising:

a container means for containing the surgical sponges, an opening in the container means above a receptacle means for receiving the surgical sponges;

scanner means for detecting when one of the surgical sponges passes through the opening;

detecting means for automatically determining the dry weight of the surgical sponges which have passed through the opening since a predetermined time by detecting the indicating means on the sponges;

calculating means for automatically determining the approximate amount of body fluid contained in the surgical sponges which have entered the container since a predetermined time by subtracting the dry weight of the sponges from the weight of the sponges including the body fluids;

first display means for displaying an indication of the approximate amount of body fluid contained in the surgical sponges which have entered the container since a predetermined time;

determining means for automatically determining the number of surgical sponges which have entered the container since a predetermined time; and second display means for displaying the number of surgical sponges which have entered the container since a predetermined time; and a non-optical scanning means for detecting surgical sponges inadvertently left in a patient during surgery. Preferably, different types of surgical sponges are received by the container, the detecting means is capable of distinguishing between multiple types of surgical sponges, even those sponges of different types but similar weights, and the second display means displays the number of each type of sponge which is received. Preferably, the first display means indicates, with an accuracy of ±0.1%, the exact amount of body fluids contained in the sponges which have entered the container since a predetermined time. Preferably, the detecting means comprises a non-optical scanner means. Preferably, the non-optical scanner means can read an indicating means on the sponges even when the indicating means is covered with blood or other body fluids. Preferably, the non-optical scanner means can simultaneously read indicating means on all sponges with its read range and properly identify each sponge, and display the total number of sponges of each type.

It is object of the present invention to provide a system including surgical sponges which can be detected non-optically and a device which will detect these surgical sponges, regardless of size and location in a patient's body, during surgery with a high degree of accuracy.

It is another object of the present invention to provide a method of detecting surgical sponges non-optically, regardless of size and location in a patient's body, during surgery with a high degree of accuracy.

It is also an object of the present invention to provide a device which will detect surgical sponges, regardless of size and location in a patient's body, during surgery with a high degree of accuracy.

It is an object of the present invention to provide a device which will automatically count surgical sponges, regardless of size, during surgery with a high degree of accuracy.

It is a further object of the present invention to provide, in a device of this type, in addition to means for giving a running count of sponges, means for simultaneously weighing sponges and instantly and accurately calculating the amount of blood contained in those sponges.

Another object of the present invention is to provide a device which collects soiled surgical sponges and facilitates their disposal with minimal handling.

BRIEF DESCRIPTION OF THE DRAWING

For a further understanding of the nature, objects, and advantages of the present invention, reference should be had to the following detailed description, read in conjunction with the following drawings, wherein like reference numerals denote like elements and wherein.

PARTS LIST

The following is a list of suitable parts and materials for the various elements of the preferred embodiment of the present invention.
1 identification tag (indicating means) on sponge 2
2 sponge
3 opening in apparatus 30 for sponges 2
4 control unit (CPU)
5 display panel
6 reader (scanner)
7 reader electronics
8 disposable bag
9 door
10 weighing scale
11 rechargeable battery
12 shelf for extra bags 8
13 wheels
14 retractable electrical cord
15 wiring interconnecting the reader electronics 7 and the reader 6
16 wiring interconnecting the reader electronics 7 and the control unit 4
17 wiring interconnecting the reader electronics 7 and the battery 11
18 wiring interconnecting the control unit 4 and the scale 10
19 wiring interconnecting the battery 11 and the scale 10
20 wiring interconnecting the battery 11 and the control unit 4
21 bag rack
22 handle for door 9
23 radio waves
30 automatic surgical sponge counter and blood loss determination apparatus
31 sloped sides of receptacle 32
32 receptacle
33 label
40 hand-held RF reader (Trovan Model LID 500 hand-held reader or Tiris Model RI-HHU-WxDG hand-held reader, for example)
41 red indicator light on reader 40
42 green indicator light on reader 40
43 LCD (liquid crystal display) readout on reader 40
44 antenna of reader 40
45 power trigger of reader 40
51 sponge type and quantity display screen
52 blood-loss display screen
53 battery charge indicator
54 on-off switch
55 alarm light
80 surgical site
81 wound
82 patient
85 surgeon

DETAILED DESCRIPTION OF THE PREFERRED EMBODIMENT

The first embodiment of the present invention, automatic surgical sponge counter and blood loss determination apparatus 30, is shown in FIGS. 1 through 5.

The device (See FIG. 1) takes the place of a kickbucket which is now in use in operating rooms around the world. It is mobile (mounted on wheels 13, powered by rechargeable battery 11), compact in size (30"×18"×18", for example) and easy to operate. During an operation all surgical sponges 2 are deposited into the apparatus 30 by dropping them into a receptacle 32 having sloped sides 31 leading to an opening 3 at the top of apparatus 30. Receptacle 32 preferably has dimensions of 15" by 16", more preferably has dimensions of 16" by 18", and most preferably has dimensions of 18" by 18". The top of receptacle 32 is preferably about 20–40" above the floor, more preferably about 25–35" above the floor, and most preferably about 30" above the floor. Opening 3 preferably has dimensions of from 4" by 5½" to 6½" by 8½", and more preferably has dimensions of 5½" by 7".

To increase the chance that a sponge tossed at the apparatus of the present invention will land in receptacle 32, receptacle 32 is preferably rather large. To reduce evaporation from bag 8 and to make the scanner 6 relatively close to the sponges 2 passing through the opening 3, opening 3 is preferably relatively small. Preferably, the ratio of the size of opening 3 to the size of receptacle 32 is rather small.

As the sponge 2 passes through the opening, a reader 6 reads what type of a sponge has entered (Lap, Mini-Lap, Raytec, etc.) from a radio frequency tag 1 attached to the sponge 2. The control unit 4 receives data from the reader 6 along with data from the scale 10 and then processes this information using preprogrammed software. The final output is displayed on the display panel 5: a readout of the number of sponges contained in the unit, broken down by type, is displayed on screen 51; the amount of blood and other bodily fluids contained in the sponges is displayed (preferably in cubic centimeters) on screen 52. This amount will be calculated by the control unit 4 using a formula based on the weight of the sponges 2 soiled, minus the weight of the sponges 2 dry (different size sponges 2 have different dry weights; the dry weights of different sponges is preferably pre-programmed into the software so that nurses will no longer have to do this manually).

Figure 3:
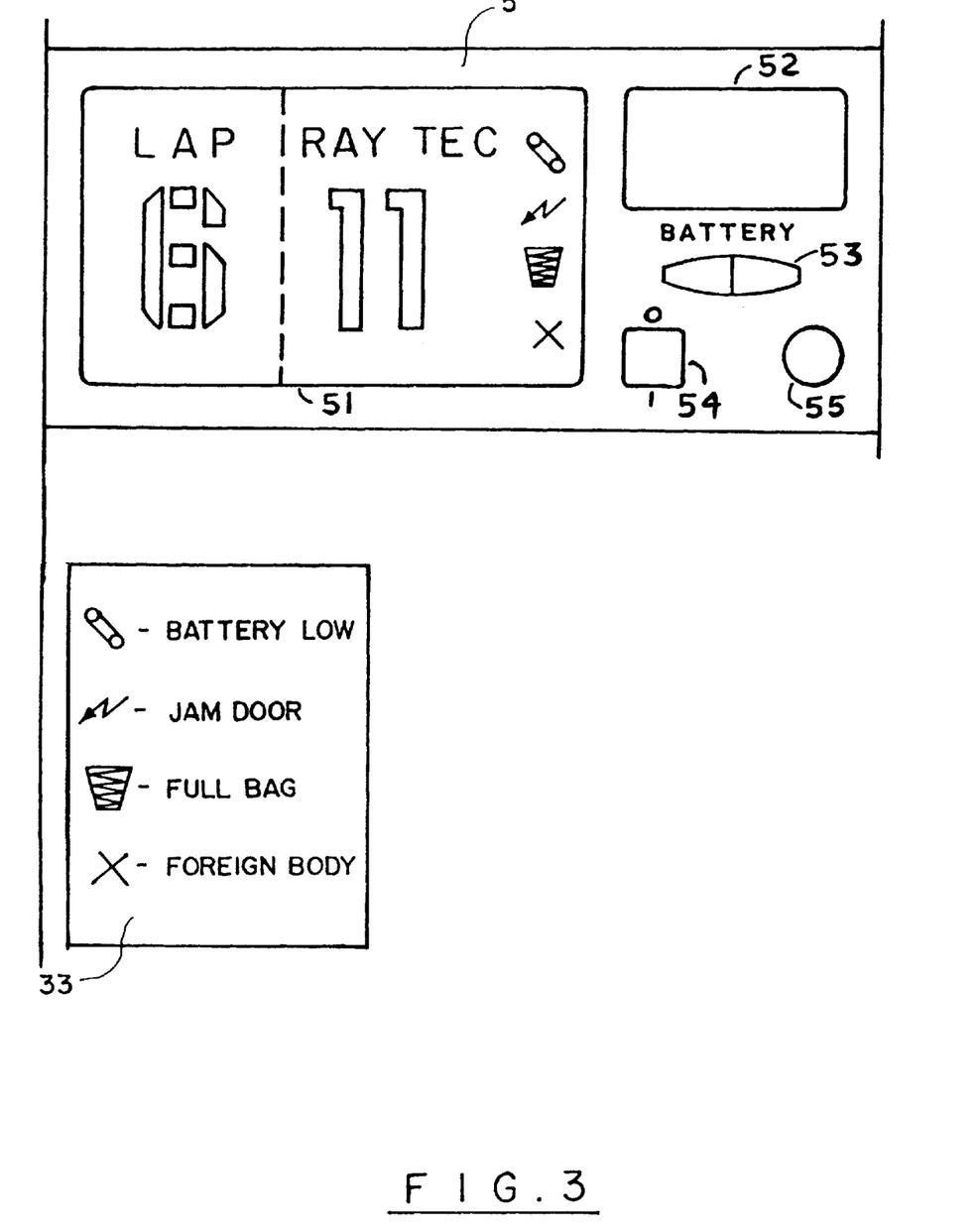
FIG. 3 is a detail of the control panel and display of the first embodiment of the apparatus of the present invention.
Figure 4:
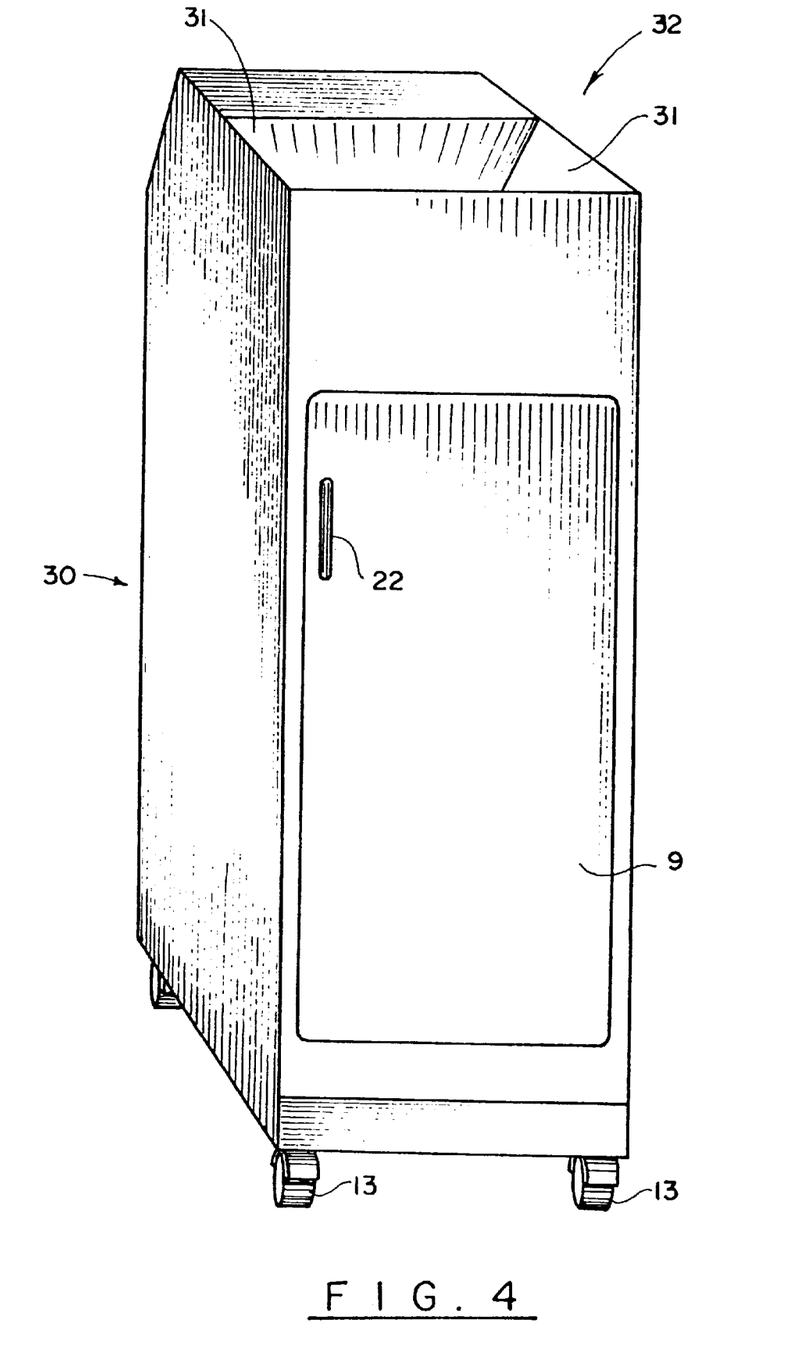
FIG. 4 is a rear view of the first embodiment of the apparatus of the present invention.
Figure 5:
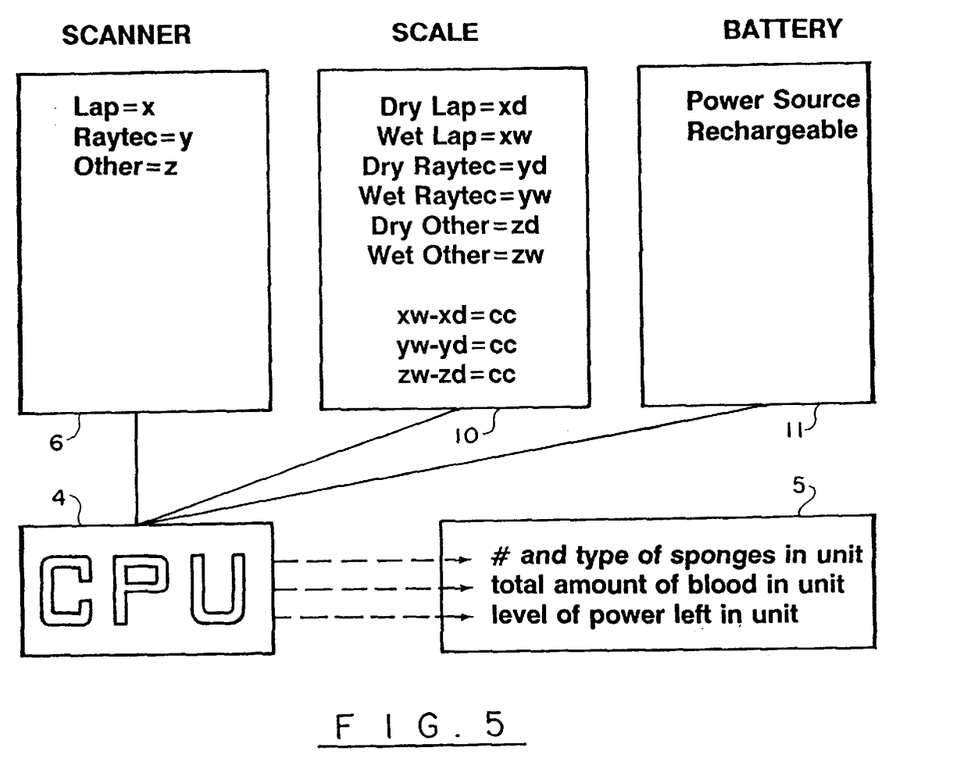
FIG. 5 is a block diagram indicating the input and output of the CPU of the first embodiment of the apparatus of the present invention.
Figure 6:
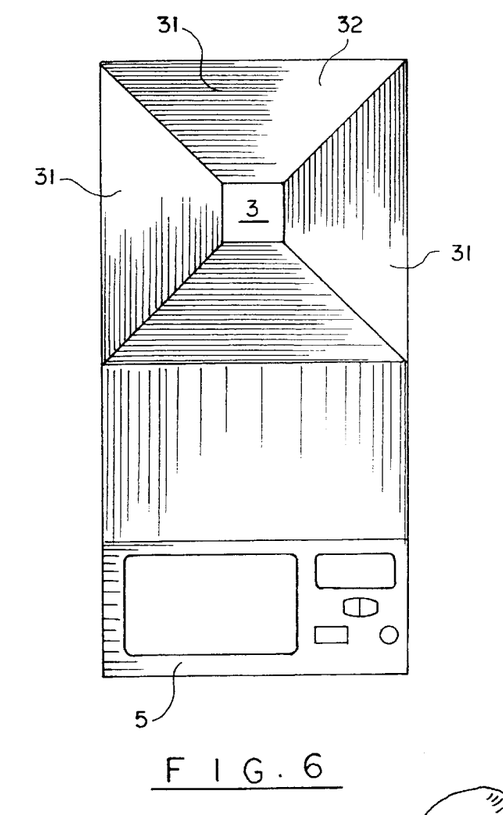
FIG. 6 is a top view of the first embodiment of the apparatus of the present invention.

The battery charge is indicated on battery charge indicator 53, with the left side being red and lighting up if the charge is low, and with the right side being green and lighting up if the charge is sufficient. An on-off switch 54 lights up with a green light when the power is on.

Label 33 displays the symbols and explanations for a number of alarm conditions which cause alarm light 55 to light up. When one of the conditions displayed on label 33 occurs, the appropriate symbol flashes in screen 51. The conditions include a low battery charge condition, a jammed door, a fill bag, and the presence of foreign objects (needles, hypos, cottonoids, bovie tips, etc.) inside of the device.

Figure 1:
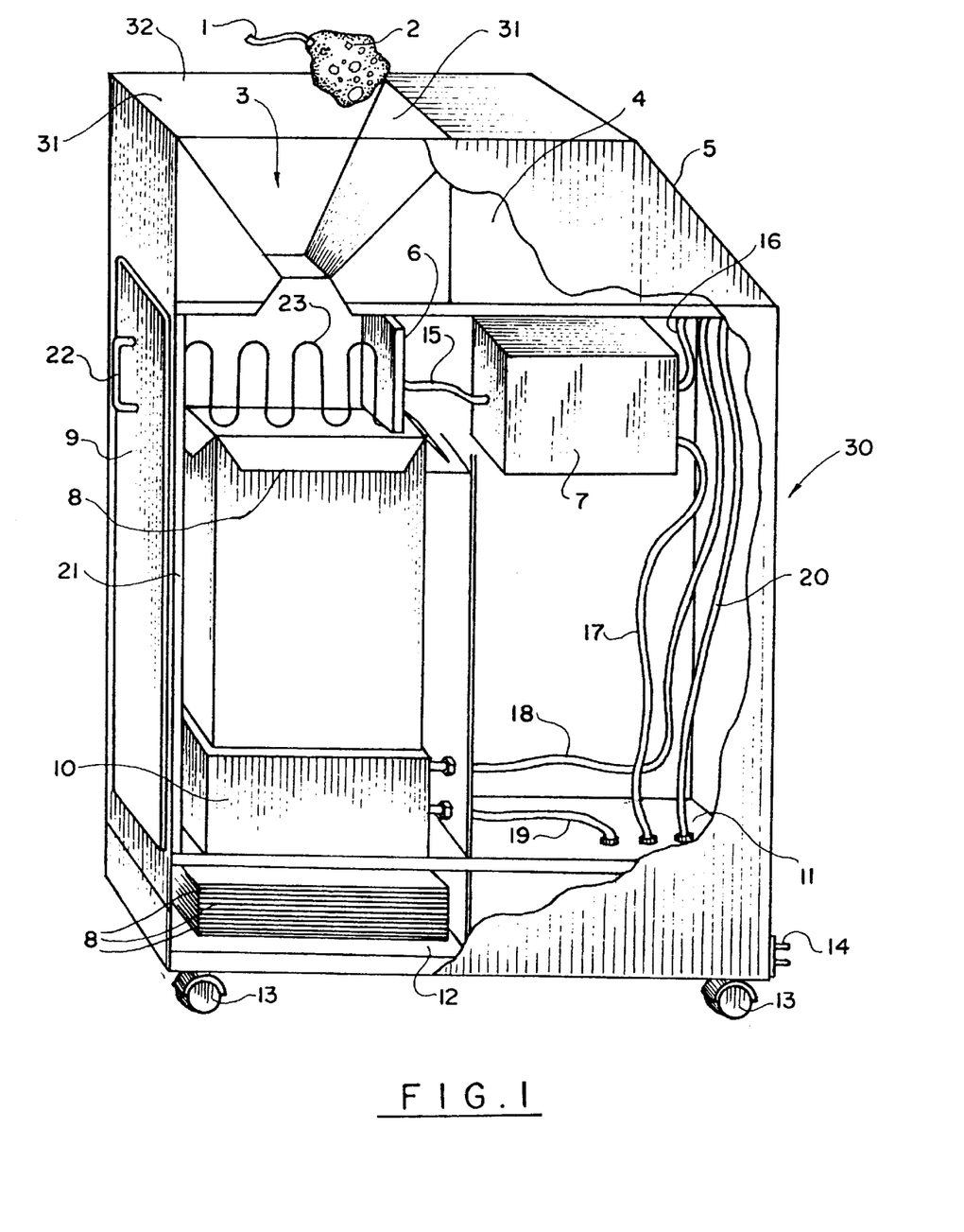
FIG. 1 is a cutaway, side view of a first embodiment of the apparatus of the present invention.
Figure 2:
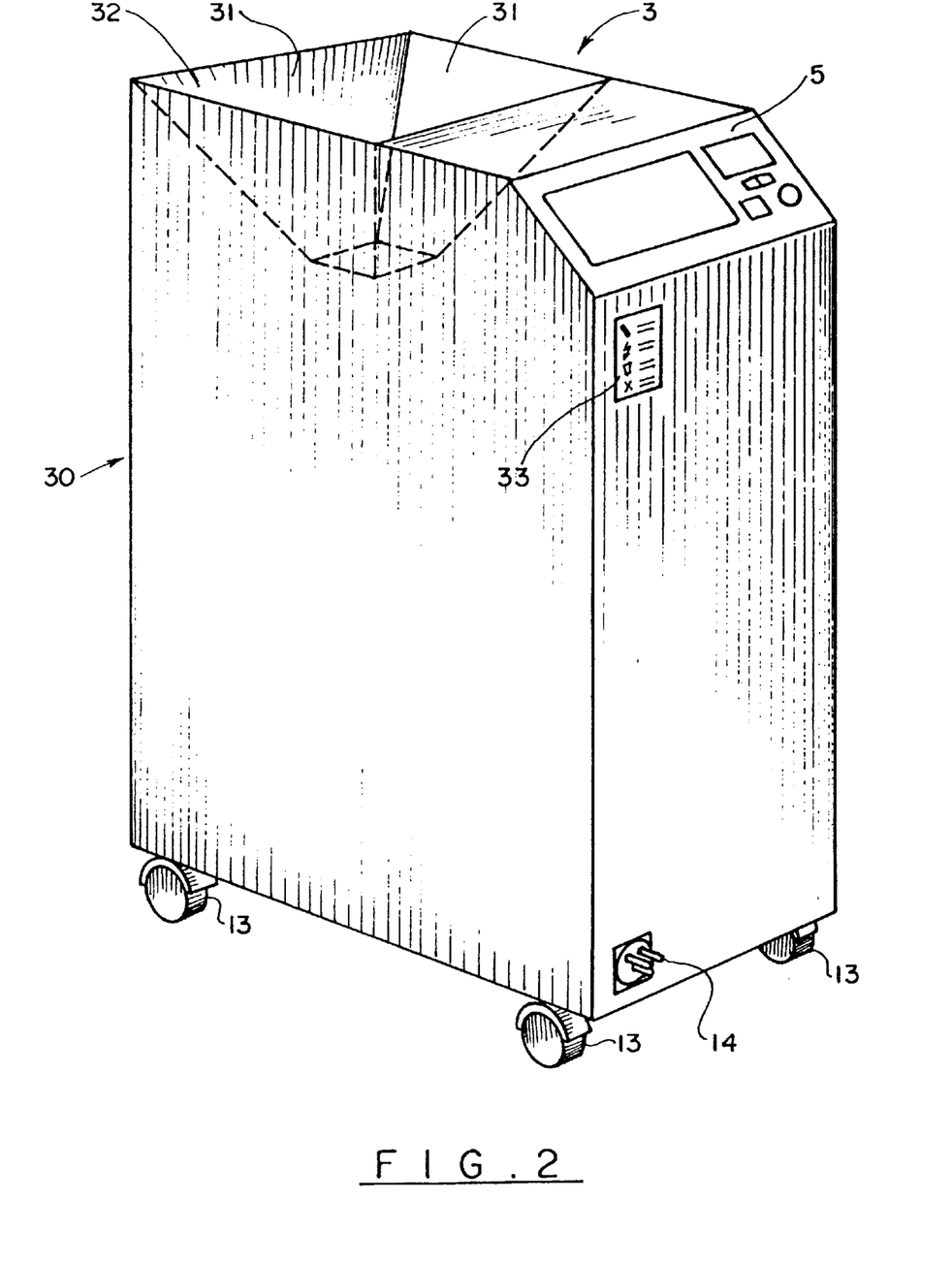
FIG. 2 is a perspective view of the first embodiment of the apparatus of the present invention.

Once the sponge 2 passes the reader 6 it is deposited in a disposable bag 8 which is suspended from a rack 21 connected to a scale 10. The scale 10 weighs the contents of bag 8 and sends this data to the control unit 4 as mentioned above to be processed. Apparatus 30 can be programmed to alarm once a predetermined number of sponges 2 has been reached or when the bag 8 is fill. The disposable bag 8 can then be removed through a rear door 9 and replaced with a new bag 8. A compartment 12 to store extra bags is provided. The memory of control unit 4 will continue to give a running count of sponges 2 as well as estimated blood loss amount for the duration of the entire surgical procedure. Once the operation is complete and all counts have been verified, the device 30 can be cleaned very easily, reset and ready for the next case. Because of the small size and mobility of apparatus 30, it can be moved from room to room effortlessly.

Tags 1 can preferably endure temperatures of up to about 400 degrees Fahrenheit (about 200 degrees Centigrade) to allow them to be autoclaved.

At the end of the day the device 30 can be plugged with plug 14 into an electrical outlet and recharged for the next day's use. Additional features can include: a gauge which indicates battery status by displaying the remaining life of the battery in hours and a low battery alert alarm. The battery 11 is rechargeable during operation of the device 30.

While other technologies may be available, radio frequency is believed to be the optimal technology. Radio frequency tags are preferred to other identifying means because they do not depend upon light for detection—they can be detected even when completely covered with blood. Other identifying means which can be attached to surgical sponges and which does not depend upon light for detection could be used.

Indala Corporation, San Jose, Calif. has a brochure dated 1993 (attached and hereby incorporated by reference) which discloses an RF technology, purportedly covered by U.S. Pat. No. 4,818,855 and Canadian Patent No. 1253591, which the inventors contemplate using with the present invention. These patents are also incorporated by reference. Specifically, when the hand-held reader is not to be used, the preferred tag to use with the present invention is the Indala IT-52 Mini Disc Tag. The IT-52 is a transfer-molded, chemical resistant plastic disk 7/16" (11 mm) in diameter by 1/8" (3 mm) thick. It has a weight of approximately one gram. The preferred reader 6 for the apparatus of the present invention is the Indala IR-50; the IR-50 can read the IT-52 at a range of 4" (100 mm). The tag 1 is preferably attached to a surgical sponge by being sewn onto the sponge with and where the radio opaque marker is currently attached. The information which tag 1 contains is preferably simply a number—in the control unit 4, that number is associated with information (such as brand name, dry weight, and size) about the sponge 2 to which tag 1 is attached. Control unit 4 is pre-programmed with information about each different type of sponge which is used with apparatus 30. This sort of system may be more economical than one in which all information about the sponge is contained in the tag 1, and may make it easier to convert from one tag technology to another.

ADVANTAGES OF THE DEVICE OF THE PRESENT INVENTION

The sponge count is an essential part of operating room procedure. It not only assures patient safety, but it also provides the medical team with an ongoing estimation of blood loss. Current methods for handling surgical sponges are antiquated and inadequate in today's modern and potentially dangerous operating room environment. Even in the newest hospitals, sponges are still counted and weighed manually. These procedures are time-consuming, prone to human error and unnecessarily expose medical staff to blood contact. The present invention addresses these shortcomings by integrating all sponge-related functions into one fully automated unit. The present invention is different from prior art on the subject of sponge management in that it has the ability to distinguish between different types of sponges, maintain a running count of each type of sponge being used in a given procedure, and automatically calculate the amount of blood contained in those sponges, instantly. These improvements will dramatically affect sponge management in the areas of safety, sponge counts and blood measurement.

Safety: The present invention will have its biggest impact in the area of increased safety for medical staff. Exposure to bloodborne pathogens will be significantly reduced due to less handling of soiled sponges and the closed environment of the device. Currently, soiled sponges are handled several times by different members of the medical team. They are first handled by scrub personnel. Next they are counted by the circulating nurse. They are then bagged, weighed when necessary, and if a count is incorrect, they are removed from the bags and recounted. Finally, an orderly has to clean the area where the sponges are handled. With the present invention, soiled sponges will only be handled once by the staff member who deposits the sponge into the device. The device will then do the counting, estimate blood loss amount and store the sponges in a disposable bag. This will be done in a closed environment as opposed to an open bucket thereby reducing airborne contamination and also reducing the time spent cleaning areas where sponges are counted. Because the disposable bag is enclosed inside of the device, less bloodborne pathogens can escape due to evaporation.

Sponge Counts: The present invention will increase the accuracy of sponge counts by eliminating human error and providing a running count of sponges already used. It will give a visible readout of all different types of sponges used during a given procedure. This is important because it allows the staff to constantly check counts throughout the procedure. An increase in accuracy reduces the chances that a sponge will be left in a patient. This increases safety for the patient and reduces the time that is spent recounting sponges, thus reducing total count time. Also, because the device contains a disposable bag, staff will no longer have to bag sponges manually, thus saving time. The technology that is preferred to be used to do the scanning (radio frequency) is extremely accurate (fewer than 1 error out of 1,000,000).

Estimated Blood Loss Measurement: The present invention has the ability to weigh soiled sponges, automatically compute blood loss, and give a constant visible readout of that amount. This is an important feature for several reasons. A constant readout is valuable to anesthesiologists and surgeons who use this information as one component in estimating total blood loss for a given procedure. Instant information is helpful when ordering blood components and reduces guessing on blood loss amount. In the case of small children or infants this information is critical. Currently, surgeons and anesthesiologists have to estimate the amount of blood loss by sight and the manual weighing of sponges, which is done by the circulating nurse. Besides the time saved in weighing and doing a manual calculation of blood loss, the device reduces human error in the calculation. This increases safety for the patient. Also, a reduction in time spent handling soiled sponges reduces staff exposure to blood.

The apparatus of the present invention counts surgical sponges (Laps, Raytecs, etc.) with a high degree of accuracy. It constantly calculates the amount of blood and other bodily fluids in the sponges. It includes a rechargeable battery 11 and can include a visible battery gauge which displays the remaining life of the battery in hours. It has an alarm which goes off when the charge in the battery 11 drops below a predetermined amount. The battery 11 is rechargeable during operation of device 30.

The container 30 of the present invention is compact in size, and can have exemplary dimensions of one foot by two feet, which is bigger than a standard a kick bucket.

Container 30 is mobile and durable. It can distinguish between different types of sponges (Laps, Raytec, Mini-Laps, etc.). It includes disposable bags. It is simple and easy to operate, and has the operating instructions on its face. Disposable bags 8 have a capacity of at least forty sponges when properly installed upon rack 21 of device 30.

Container 30 can interrupt the count and maintain the sponge count and blood loss amount. An alarm sounds when it is time to change bag 8 (that is, when a predetermined number of sponges have entered container 30 since the last change of the bag). An alarm could also sound when a foreign object is present in the container 30.

The device 30 of the present invention can read tags 1 even when the tag 1 is hidden or covered with blood. Device 30 is easily and quickly cleaned. It is water-resistant and does not have to be sterile.

The reader 6 can preferably detect up to six tags 1 at one time. It preferably can detect foreign objects, such as needles, hypodermic needles, cottonoids, bovie tips, etc. The count can be interrupted to allow the inspection of foreign matter.

The ability to distinguish between different types of sponges helps to accurately estimate the amount of blood lost during surgery. For example, Raytec sponges weigh, when dry, about five grams. Lap sponges weigh, when dry, about 20 grams. When soaked with blood and/or other bodily fluids, Raytec sponges can weigh up to about 50 grams and Lap sponges can weigh up to about 120 grams. Suppose, for example, that forty sponges are used during an operation, and half are Raytec sponges and the other half are Lap sponges. The total weight of blood and sponges is about 1,500 grams, with 500 grams representing the dry weight of the sponges and 1,000 grams representing the weight of the blood and other bodily fluids (1,000 cc's of fluid). If all of the sponges were treated as being Lap sponges, then the calculation would improperly treat 300 grams of blood as dry weight of the sponges. Thus, the amount of estimated fluid lost would be improperly reduced by 300 grams (300 cc's of blood). The weight of tags 1 is not being considered, since tags 1 weigh the same whether attached to a Raytec sponge or to a Mini-lap sponge.

Figure 7:
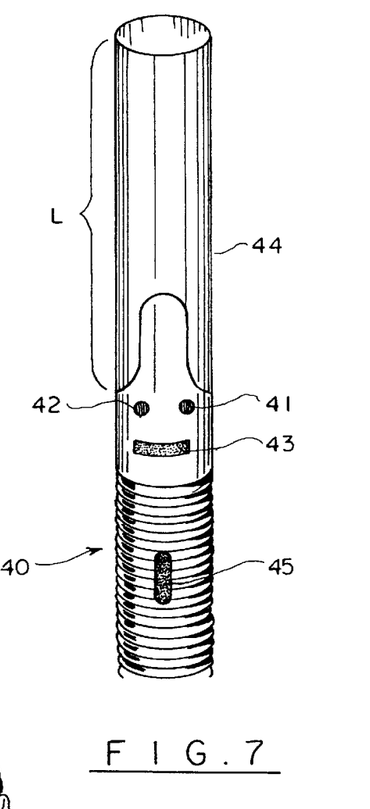
FIG. 7 is a perspective view of the preferred embodiment of the present invention.
Figure 8:
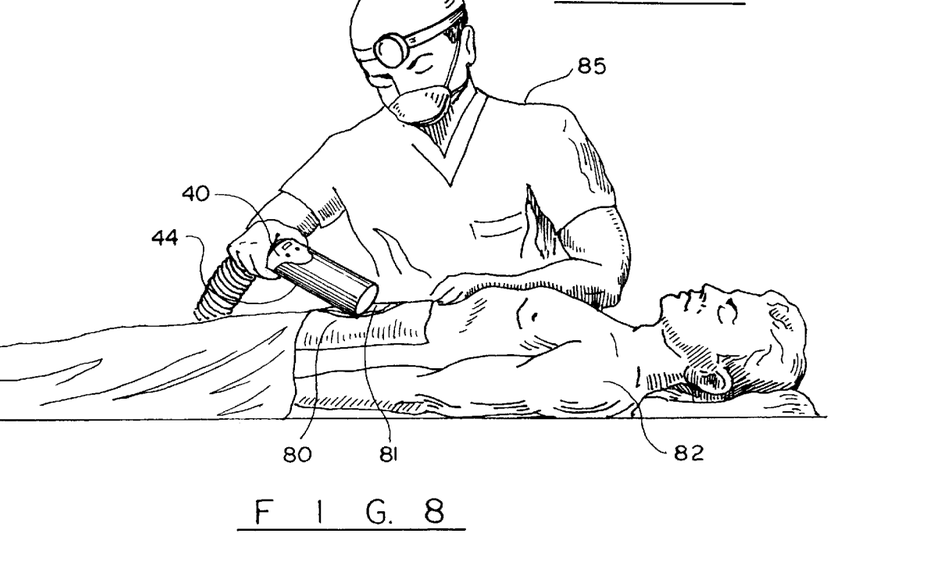
FIG. 8 is a top view of the preferred embodiment of the method of the present invention.

The preferred embodiment of the present invention is a hand-held surgical sponge detection system shown in FIGS. 7 and 8. A hand-held RF reader 40 will be used by surgeons 85 to detect the presence of surgical sponges 2 in the body cavity at the time of closure during a surgical procedure (see FIG. 8). The Hand-held RF reader 40 will be passed over the surgical site 80 prior to the closing of the cavity by the surgeon 85. It will then identify any sponges 2 which may have been inadvertently left in the wound, thus preventing the retention of sponges 2 inside of the patient. This hand-held RF reader 40 can be used during all surgical procedures and will eliminate the dangerous and time-consuming task of manually counting and bagging of soiled sponges 2. This device is small in size, (preferably smaller than 10 inches in length×7 inches in Width×10 inches in Height, excluding the antenna 44), light-weight, (less than three pounds) and battery operated. It can be used alone or as part of the "Automatic Surgical Sponge Counter and Blood Loss Determination System" described in co-pending International Application Number PCT/US95/09094 and U.S. patent application Ser. No. 08/286,413. The length L of antenna 44 is preferably one to 28 inches, more preferably five to 25 inches, and most preferably ten to 14 inches. Antenna 44 can be, for example, 14 inches long.

When a surgeon 85 is ready to begin closure of the body cavity, the hand-held RF reader 40 will be passed over the surgical site80. A red light 41 on the hand-held RF reader 40 indicates the presence of a sponge 2 in the wound 81 and a green light 42 indicates that no sponges 2 are in the wound 81. If a sponge 2 is detected, an optional LCD readout 43 on the display can indicate what type of a sponge 2 is in the cavity (Laparotomy, Mini-Laparotomy, Raytec, etc.). Before the device 40 is handed to the surgeon, it will be placed in a sterile plastic bag (not shown) to prevent blood from getting on the device 40. After the hand-held RF reader 40 is used, it will be removed from its protective bag, cleaned and stored until its next use. If necessary, it may be possible to sterilize the device 40. The hand-held RF reader 40 can be mounted on the wall in the operating room for easy accessibility or if the room has an automatic surgical sponge counter and blood loss determination system 30, it can be mounted on this device 30. A trigger 45 is used to activate the reader 40.

There are several commercially available hand held readers on the market today which could be used with slight or no modifications. These modifications could include a redesign of the handle to adjust for the ergonomic demands of the operating room and if necessary, a redesign of the reader antenna to increase the read range of the reader. Two examples of commercially available hand held readers which could be used are: 1) the Trovan®—Model LID 500 hand held reader which is manufactured by AEG/Telefunken and 2) the Tiris™—Model RI-HHU-WxDG hand held reader manufactured by Texas Instruments. The invention disclosed herein can be demonstrated now by using animal carcasses, veterinary surgery or by having a person lay on top of an RF tag 1.

Because of its relatively large read range, a Trovan®—Model LID 504C panel reader (not shown, manufactured by AEG/Telefunken) could advantageously be used as the hand-held reader 40, but its dimensions exceed the preferred dimensions for reader 40. A Trovan®—Model LID 504C panel reader could be placed under the patient 82 during the entire surgery, or just at the end.

The tags of the present invention and the readers of the present invention could be, for example, those described in the brochures in the Information Disclosure Statement accompanying this patent application, either as described in those brochures or modified as suggested herein.

The hand-held RF reader 40 will totally eliminate the chance of a surgical sponge 2 being retained inside of a patient during surgery. As a result, the labor intensive, dangerous, and error-ridden methods currently being used in operating rooms worldwide to account for soiled surgical sponges will also be eliminated. By having the ability to automatically identify these sponges 2 at any time during surgery, especially at the time of closure, an increased level of safety for both patients and staff will be realized, a drastic increase in the productivity of nursing staff will occur, procedures will be streamlined, and liability for hospitals, surgeons and nurses will be reduced. Sponges are the most time consuming and dangerous foreign bodies to keep track of during surgery as well as the item most often retained.

The sponge management system (automatic surgical sponge counter and blood loss determination apparatus) 30 of the present invention is a fully automated medical device which will manage all sponge-related functions in an operating room. This small, mobile unit 30 will handle the counting of all sponges 2 used during surgery, regardless of the size of those sponges 2. It will also bag, weigh and automatically compute the amount of blood contained in those sponges 2, instantly. A liquid crystal display screen will display a readout in CC's of estimated blood loss amount contained in the unit, as well as a running count of all types of sponges 2 deposited. The hand-held RF reader 40 will be mounted on device 30, to be used at the time of closure to assure that no sponges 2 have been retained in the body cavity. Device 30 is particularly well suited for procedures in which above-average blood loss occurs such as cardiac, transplants, obstetrical, etc. and procedures involving small children or infants where blood loss monitoring is critical.

During surgery all soiled surgical sponges 2 will be deposited directly into device 30 through an opening 3 at the top of device 30. As the sponge 2 passes through the opening 3, a stationary reader 6 will read what type of sponge 2 has been entered (Laparotomy, Mini-Lap, Raytec, etc.) from a small radio frequency tag 1 which has been securely attached to the sponge 2 by the sponge manufacturer. The control unit 4 will receive data from the reader 6 along with data from the on-board scale 10 and then process this information using preprogrammed software. The final output will be displayed on the display panel; a readout of the number of sponges 2 contained in the unit, broken down by type, and the amount of blood contained in those sponges 2 in CC's. The unit 30 will calculate blood loss by using a formula based on the dry weight of the sponges 2. Different size sponges 2 have different dry weights. This data will be programmed into the software so that nurses will no longer have to do this manually. Once the sponge 2 passes the reader 6, it is deposited into a removable disposable bag 8 which is suspended from a rack attached to a scale. The scale 10 weighs the bag 8 and sends this data to the control unit 4 to be processed. Device 30 can be programmed to alarm once a predetermined number of sponges 2 has been deposited, a predetermined weight has been reached, or when the bag 8 is full. It is anticipated that the bag will be able to hold up to forty or more sponges 2. The disposable bag 8 can then be easily removed, sealed and replaced with a new bag. The unit's memory will continue to give a running count of sponges 2 as well as estimated blood loss for the duration of the entire procedure. The hand-held RF reader 40 can be mounted on the side of device 30, easily accessible to medical staff. The hand-held RF reader 40 can be used to make absolutely sure that no sponges 2 have been left in the patient before closure. Once the procedure is complete, the device 30 can be easily cleaned, reset and ready for the next case. The device 30 will be mobile, (mounted on wheels, powered by a rechargeable battery 11), compact in size, (30" Height×18" Width, e.g.) and extremely easy to operate. Because of the units small size and mobility, it can be easily moved from room to room effortlessly. At the end of the day, the device can be plugged into an electrical outlet and recharged for the next day's use.

In the United States and many other industrialized nations worldwide, hospitals are facing tremendous pressure by both the public and private sectors to reduce costs while at the same time delivering high quality patient care. Hospital administrators must begin looking at innovative ways to wring out excessive costs through the use of automation and job redesign. Both of the devices discussed will give operating room managers the opportunity to significantly reduce costs by automating, streamlining and eliminating many of the dangerous and time consuming tasks currently involved in sponge management during surgical procedures. Significant productivity gains can be expected as the implementation of RF technology reduces labor time and allows for a more efficient utilization of staff and thus a reduction in payroll costs. Safety for both patients and staff will be significantly increased by eliminating the manual counting, bagging and weighing of soiled surgical sponges 2. This dangerous, labor intensive task will be replaced by a handheld RF reader 40 that will totally eliminate any chance of a sponge 2 being retained in the patient. Sponges left in patient are one of the leading causes of malpractice lawsuits and insurance claims following surgery. Blood exposure for medical staff will be drastically reduced by eliminating the handling of soiled sponges.

The Hand-held RF reader 40 and device 30 will improve productivity and help bring down labor costs. Labor costs account for 32% of the typical surgery department's budget. Current methods of sponge management rely on the manual counting, bagging and weighing of soiled surgical sponges. This task is almost always performed by a Registered Nurse because of patient safety and liability issues involved. In medium to heavy blood loss cases, a significant amount of labor time is committed to this task. For a two to three hour procedure such as a prostatectomy, twenty to thirty minutes of nurse labor is required to manually account for the fifty to sixty sponges utilized during the procedure. In larger cases such as cardiac, transplants, vascular, abdominal, trauma, and obstetrical, for example, the amount of labor time is even greater. This labor is expensive. The typical Registered Nurse in an operating room has an annual salary of between $35,000 and $45,000. The Hand-held RF reader 40 will totally eliminate any counting of sponges regardless of procedure. Nurses will now have more time to chart and do paperwork, prepare medications, order blood components, prepare for the next case and be more attentive to the needs of the surgical team and patient. Many surgery departments are currently trying to reduce the ratio of expensive Registered Nurses to inexpensive unlicensed personnel on their staff. The hand-held RF reader 40 and device 30 will help hospitals facilitate this process by utilizing their RN staff more efficiently by having RN circulators supervise less expensive unlicensed personnel in several rooms, simultaneously.

The hand-held RF reader 40 and device 30 will increase safety for both patients and medical staff. The Hand-held RF reader 40 will totally eliminate the chance of a sponge 2 being retained in the patient and device 30 will improve the accuracy and availability of blood loss estimation in cases in which blood loss is significant or vital due to size and age of patient. These devices will also eliminate the need for staff to manually account for soiled sponges which exposes them to excessive blood exposure and ergonomic hazards such as back injuries.

The main reason for the elaborate count procedures currently used in modem operating rooms today is to prevent the retention of foreign objects such as sponges, instruments, sutures, bovie tips, etc. in the body cavity. Sponges in particular can cause severe infections and injury if left in the patient. If a sponge is accidentally retained, then all relevant members of the team can be held responsible, either individually or jointly. This includes the surgeon, the circulating nurse and the hospital. Evidence of a retained sponge being left in a patient after closure is considered proof of negligence on the part of the medical team. From a liability standpoint, when a retained sponge case is brought to court, the question is not, "Who is responsible?" but "How much is the injury worth?" Retained sponge cases usually are settled before court proceedings unless the plaintiff asks for unrealistic compensation.

Current methods for estimating blood loss in surgical sponges are inadequate because of excessive reliance on visual estimation and manual weighing of sponges. Currently, if a surgeon or anesthesiologist needs to know how much blood is contained in the sponges, he must estimate the amount by visual inspection of sponge bags. Although the individual physician may know that he or she is in the safe zone, without actually weighing the sponges, they cannot know the exact amount. In many instances, blood contained in the sponges is the only exact amount of blood loss that is unknown by physicians during surgery. In certain procedures and in the case of infants and small children, it is vital to know this amount. The surgeon may request that the circulating nurse manually weigh the sponges and calculate the amount of fluid contained in those sponges. When sponges are weighed, the circulating nurse must individually weigh each sponge before bagging and keep a running total throughout the procedure. This involves several manual calculations. This is very time consuming, prone to human error and involves excessive handling of bloody sponges. Device 30 will improve blood loss estimation techniques just discussed. It will have the ability to weigh sponges and determine blood loss contained in those sponges, instantly. This amount will be displayed on a display panel for all staff to see. This is important for several reasons. Human error in the calculation is reduced by having the device perform the calculation instead of a busy nurse. All relevant data needed for the calculation is contained on the tag and preprogrammed software in the device. The unit will use this information along with data from an internal scale to accurately determine blood loss. A constant, visible readout of this amount may increase response time when ordering blood components. In addition, device 30 will reduce guessing by surgeons and anesthesiologists on blood loss amount contained in the sponges 2. All of these improvements will increase patient safety.

Safety for medical staff will also be improved by using the Hand-held RF reader 40 and device 30. Current methods are unsafe for a variety of reasons. Exposure to blood is unacceptably high and back injuries are common. With the prevalence of Hepatitis B Virus (HBV), Human Immunodeficiency Virus (HIV), and other dangerous pathogens in today's society, blood exposure is one of the most pressing issues in the operating room today. Currently, soiled sponges are handled several times by different members of the medical team. They are first handled by scrub personnel. Next they are manually counted by the circulating nurse. They are then bagged, weighed when necessary, and if a count is incorrect, they are removed from the bags and recounted. Finally, an orderly has to clean the area where the sponges are handled. If it is a long procedure, shift changes or relief breaks can expose more personnel. With the hand-held RF reader 40 and device 30, blood exposure for the circulating nurse will be dramatically reduced. The circulator will no longer have to touch bloody sponges. Instead of several staff members handling sponges, the number is reduced to one. Regardless of which device the operating room is using, the scrub person will be the only staff member who will come in contact with soiled sponges. In those rooms using the Hand-held RF reader 40 alone, the scrub nurse or tech will deposit soiled sponges 2 directly into a garbage can. In rooms where both the Hand-held RF reader 40 and device 30 are being used together, the scrub will deposit sponges 2 directly into device 30. The unit will then count, bag, weigh and calculate blood loss. Ninety percent of blood exposure that a circulating nurse currently encounters on a daily basis comes from handling sponges. The number of staff whose blood exposure will be reduced is amplified when the people involved in shift changes and relief crews are included. The standard kickbucket, into which the used sponges are deposited now, is basically a stainless steel bucket with wheels. As the blood in the sponges evaporate, airborne contamination can occur. This is not sanitary, nor safe. Device 30 will store the sponges 2 inside the device in a removable disposable bag. This is a closed environment as opposed to the open environment of the kickbucket. In addition, nurses are constantly bending over to retrieve sponges from this bucket. This is not ergonomically sound and leads to numerous back injuries. Nurses rank fifth among occupations receiving worker's compensation claims for back injuries. These back injuries average $3,000 to $4,000 per reported injury. If a procedure uses fifty sponges, the circulating nurse will have bent over anywhere from five to fifty times in order to retrieve the sponges. In large cases, sometimes the nurse will get on her hands and knees and layout soiled sponges on the floor to get an accurate count. Device 30 will eliminate the need to bend over in order to retrieve sponges out of kickbuckets and thus will reduce the number of back injuries in the operating room. Kickbuckets will no longer be necessary in operating rooms. This should reduce the number of personnel who injure themselves by tripping over them. In conclusion, device 30 and hand-held RF reader 40 will provide a safer operating room environment for medical staff.

Usage of surgical sponges and gloves should also be reduced by using the Hand-held RF reader 40 and device 30. Currently, surgical sponges are packaged in bundles of five to help facilitate manual counting by nurse personnel. Because of sterility concerns, if a bundle is opened and only one sponge is used the other four cannot be used for another surgery unless they are re-sterilized. These sponges are usually taken home by staff and used as dust cloths and wash cloths. These sponges cost between ten and sixty-eight cents apiece. By using the hand-held RF reader 40, sponges 2 can be dispensed one at a time as needed, thereby reducing the contamination of excessive numbers of sponges. Sponge usage in the typical OR can be reduced by a conservative ten percent. Glove usage should decrease as well because a circulating nurse changes gloves several times during the course of surgery in order to manually count and bag sponges. The Hand-held RF reader 40 and device 30 will eliminate this task.

Repeat surgeries to extract retained sponges will be eliminated and all associated surgery costs will be as well. X-ray costs will be reduced as they will not be needed anymore to determine if a sponge has been retained. Typically it cost around sixty dollars for one of these operating room X-rays to be taken. This does not take into account the fifteen to thirty minutes of valuable room time which is needed, the protection measures such as lead aprons, etc. that the staff must take and the x-ray exposure to which the patient is exposed.

The following are advantages that key personnel and hospitals who utilize the present invention will realize.

For nurses, the invention: reduces or eliminates count time; can reduce liability with respect to retained sponges; reduces exposure to blood; reduces risk of infectious disease; increases accuracy of count; increases patient contact; increases attentiveness to procedure; increases attentiveness to surgeon's needs; increases attentiveness to anesthesiologist's needs; increases attentiveness to surgical tech's needs; and increases productivity by freeing the nurse for other duties.

The surgeons and anesthesiologists benefit because the present invention: increases accuracy of blood loss amount; can reduce liability with respect to retained sponges; increases response time on checking and ordering blood components; and reduces guessing on blood loss amount.

The hospital benefits from the present invention because: it helps to provide a safer environment for operating room employees due to less exposure to bloody sponges; it increases accuracy of sponge counts; when the hand-held reader is used, it can eliminate the need to count sponges; it causes a reduction in or elimination of repeat surgeries to extract sponges left in wounds; it causes a reduction in costs and risks associated with repeat surgeries; it causes an increase in productivity of the Circulating Nurse; it causes an increase in quality of patient care due to more attentive O. R. Nurse, less chance of repeat surgery due to sponge left in wound, and reduced guessing on blood loss by anesthesiologists.

While it is preferred to use radio frequency tags and an associated detector, other means for distinguishing one type of sponge from another could be used, such as an electric eye, metal indicators, color indicators. However, tags which can be detected by non-optical detecting means are preferred, because then one does not need to be concerned about the location of the tag and whether it is clean or covered with blood.

The RF tags 1 used for the present invention are preferably inexpensive, small, durable, extremely accurate and reliable with a read range of at least ten inches. The tags 1 will be fastened to the sponges 2 when the sponges 2 are being manufactured.

Due to the low cost of surgical sponges, (10 cents–70 cents apiece), any RF tag used should be obtained at a cost of less than fifty cents apiece for the project to be successful. Currently, suitable tags cost between $1–$3 per tag. The inventors believe that procurement of RF tags for between twenty and fifty cents apiece two to three years from now is a reasonable expectation given the number of tags involved, the rapid acceleration in RF tag technology and based on personal interviews with representatives of Motorola Indala of San Jose, Calif., one of the leading manufacturers of RF tags.

The tags 1 should be small so that they are unobstructive to the surgeon and easily attached at the factory. Several manufacturers have suitable tags which have diameters of less than a half inch and weigh less than 4 grams. Three possible means for attachment include; sewing the tag into the sponge, gluing and pressing between layers of material, riveting the tag onto the sponge or a combination of these methods. Any method or methods utilized must be extremely secure to avoid a tag 1 being left in a patient. If a tag 1 is accidentally left inside a human it should pose no health threat. Any tag 1 used will undergo appropriate toxicology tests conducted by an independent lab. The tags 1 will be attached to all types and sizes of surgical sponges used during surgery. This includes Laparotomy, Mini-Laparotomy, Raytec, etc. So that the sponges 2 are compatible with the device 30, each different type of sponge 2 will have a unique code which identifies the size and type of sponge 2 being tagged (a Laparotomy sponge for example). For this reason, quality control measures must be in place at the factory to ensure that the proper tag 1 is being attached to the proper sponge 2.

The tags 1 must be durable to withstand the unique rigors of the operating room environment. Currently available tags can withstand all sterilization processes used to sterilize sponges. Examples include: gamma radiation, gas concentration, vacuum, pressure and temperature. They can withstand temperatures up to 400° F. without affecting internal components.

RF tag technology is extremely accurate and reliable. As long as the tag is within the appropriate read range of the reader, a proper scan will occur. An appropriate read range required of this application for most patients is eight to fifteen inches. Several manufacturers currently have appropriate tags and readers which meet this criteria.

The last several years have seen large multinational corporations enter the Radio Frequency identification business. These companies bring large research budgets and staffs to an industry which once consisted only of small niche players. As a result, a dramatic reduction in tag costs and a increase in technological innovation have occurred over the last few years. The leading manufacturers of Radio Frequency Identification products include: Motorola, Texas Instruments, Philips Electronics, Hughes Identification, Trovan-AEG/Telefunken(Germany), as well as several smaller players worldwide.

Tags which could advantageously be used as tag 1 are the Trovan® Electronic Identification Systems Model—ID 103 transponder and the Model—ID 300 transponder. In either case, the Trovan® Electronic Identification Systems LID-500 portable reader could be used as reader 40.

Preferably, scanner 6 is a scanner which can detect and distinguish among and identify multiple sponges simultaneously, such as or similar to the I² Scanner commercially available from SCS Corporation, 10905 Technology Place, San Diego, Calif. 92127. In this manner, even if two or more sponges are dropped through opening 3 at the same time, they will be properly detected.

Preferably, reader 40 is a scanner which can detect and distinguish among and identify multiple sponges simultaneously, such as or similar to the I² Scanner. In this manner, even if two or more sponges are present in a patient, they will be properly detected and removed.

With a scanner having a large enough read range and the ability to read multiple tags simultaneously, it would be possible to put a scanner on the bottom of the container and constantly read all tags in the bag.

All measurements disclosed herein are at standard temperature and pressure, at sea level on Earth, unless indicated otherwise. All materials used or intended to be used in a human being are biocompatible, unless indicated otherwise. Also, the frequencies used are preferably biocompatible.

The foregoing embodiments are presented by way of example only; the scope of the present invention is to be limited only by the following claims.

We claim:

1. Apparatus comprising a surgical sponge made of an absorbent material for absorbing fluids during surgery and having a dry weight before being used to absorb fluids and an indicating means thereon for indicating the dry weight of the sponge, the dry weight of the sponge including the weight of the indicating means, the indicating means being readable by a non-optical scanner means.

2. The apparatus of claim 1, wherein:
   the indicating means also indicates the type of sponge on which it is located.

3. The apparatus of claim 1, wherein:
   the indicating means comprises a RF tag attached to the sponge.

4. The apparatus of claim 3, wherein:
   the RF tag does not exceed one inch in diameter and 0.20 inches in thickness.

5. The apparatus of claim 3, wherein:
   the RF tag does not exceed four grams in weight.

6. The apparatus of claim 3, further comprising a scanner means for reading the tag.

7. The apparatus of claim 6, wherein:
   the scanner means can read multiple tags simultaneously.

8. The apparatus of claim 6, wherein:
   the scanner means can read and identify multiple tags simultaneously.

* * * * *